United States Patent [19]

Takano et al.

[11] Patent Number: 5,110,738
[45] Date of Patent: May 5, 1992

[54] MONOCLONAL ANTIBODY CAPABLE OF RECOGNIZING ARTERIOSCLEROTIC LESIONS AND AGENTS FOR DETECTING AND TREATING ARTERIOSCLEROSIS

[75] Inventors: Tatsuya Takano; Ryoichi Hashida, both of Tokyo; Keiji Nakagami, Kanagawa; Junji Kimura, Tokyo, all of Japan

[73] Assignee: Research Development Corporation of Japan, Tokyo, Japan

[21] Appl. No.: 132,687

[22] Filed: Dec. 14, 1987

Related U.S. Application Data

[63] Continuation-in-part of Ser. No. 801,712, Nov. 26, 1985, abandoned.

[30] Foreign Application Priority Data

Nov. 30, 1984 [JP] Japan ................. 59-252013

[51] Int. Cl.$^5$ .............. C12N 15/00; C12N 5/00; G01N 33/577; C07K 15/14
[52] U.S. Cl. .............. 435/240.27; 435/172.2; 436/548; 530/387; 530/809; 935/95; 935/103; 935/106
[58] Field of Search .............. 435/7, 240.27, 172.2; 436/548, 811, 513; 530/353, 359, 387, 809; 935/106, 110, 103, 95

[56] References Cited

FOREIGN PATENT DOCUMENTS 0189688  6/1986  European Pat. Off. .

OTHER PUBLICATIONS

Roessner et al., Virchows Arch (Germany, West), vol. 412(2), pp. 169-174, 1987.
Glukhova et al., Tissue cell, vol. 19(5), pp. 657-663, 1987.
Tsukada et al., Arteriosclerosis, Nov.-Dec. 1986, vol. 6(6), pp. 601-613.
Gown et al., Am. J. Pathol., vol. 125(1), pp. 191-207, 1986 (Oct.).

*Primary Examiner*—Esther M. Kepplinger
*Assistant Examiner*—Florina B. Hoffer
*Attorney, Agent, or Firm*—Jones, Tullar & Cooper

[57] ABSTRACT

The present invention is concerned with a monoclonal antibody capable of preferentially recognizing arteriosclerotic lesions and prepared from a hybridoma obtained by fusing myeloma cells and cells capable of producing antibodies against arteriosclerotic lesions, such as spleen cells, peripheral lymphocyte of thymus and peripheral vascular cells, the antibody can be to use as an agent for detecting the presence of arteriosclerotic lesions and for treating arteriosclerosis.

8 Claims, 12 Drawing Sheets

FIG. 12 DISTRIBUTION OF ANTIGENIC MATERIAL ON A LINEAR SUCROSE DENSITY GRADIENT OF WHHL RABBIT SERUM

MONOCLONAL ANTIBODY CAPABLE OF RECOGNIZING ARTERIOSCLEROTIC LESIONS AND AGENTS FOR DETECTING AND TREATING ARTERIOSCLEROSIS

This is a continuation-in-part of co-pending application Ser. No. 801,712 filed on Nov. 26, 1985 now abandoned.

BACKGROUND OF THE INVENTION

1. Field of the Invention

The present invention relates to monoclonal antibodies and an agent containing the same, more particularly, the present invention pertains to a monoclonal antibody capable of preferentially recognizing arteriosclerotic lesions and bonding thereto and an agent for detecting and treating arteriosclerosis, containing at least one of such monoclonal antibodies.

2. Description of the Prior Art

The atherosclerosis is a localized sclerogenous lesion developed principally in large or middle sized arterias such as abdominal aorta, coronary artery, encephaloartery, renal artery, cerebral artery and is a major cause for various kinds of infarction such as myocardial infarction, cerebral infarction. The reason why such diseases are caused has not yet been demonstrated clearly. It can be said that, in the case of aorta, a normal aorta has the three layer-structure comprising an internal membrane (tunica intima) composed of endothelial cells, a tunica media composed of the elastica and the smooth muscle of the tunica media and a tunica externa composed of elastica. In this respect, it has been reported that the following materials are accumulated therein. As the materials accumulated, there may be mentioned such as lipids, for example, cholesterol ester, phospholipids; mucopolysaccharides; blood components such as apo-LDL (low density lipo-protein) which is a main protein of LDL in plasma; fibrous tissues or the like.

As is well known, the formation of a hypertrophic portion is one of the most characteristic properties of the atherosclerosis and it has been reported that the following phenomena are taken place at that portion:
(i) the migration and proliferation of smooth muscle cells of the tunica media;
(ii) the formation of foam cells taking up a large amount of lipids therein;
(iii) the deposition of lipids at the exterior of cells;
(iv) the formation of the thrombus; etc.

The diseases caused due to the presence of the atherosclerosis, such as coronal arteriosclerosis, arteriocapillary sclerosis are developed in even younger people and gradually proceed. Moreover, when the disease is realized, the lesion thereof is established and causes patients to die in the worst case. Therefore, it seems to be more preferable to detect the presence of such lesions in the earliest stage and regress atherosclerosis. For this purpose, it is needed to have an excellent method for detecting the development of these diseases in the human body, with high accuracy and safety.

As a conventional method for detecting diseases caused by atherosclerosis, for instance, arteriosclerosis, there have been proposed (i) an echography technique in which the proliferation velocity or the reflective waves of ultrasonics is used to detect the presence of lesions or (ii) an angiography technique in which an angiogram obtained is analyzed to detect the presence of lesions. In these methods, the human body is directly examined. While, as indirect methods for diagnosis, there may be mentioned such as a method comprising collecting blood from a human body to be examined, analyzing the blood to obtain information on the amount of cholesterol and lipoprotein and on the coagulative factors and then estimating the probability whether arteriosclerotic lesions are present or not.

However, the method (i) is not sufficient in its accuracy because of its low resolution and the method (ii) needs a skilled person for operating the machine since it contains complicated operations for driving the same and possibly causes damage on the body of the patients examined. In addition, the latter indirect method also has disadvantages such that the accuracy thereof is not high enough to determine whether the person examined suffers from such disease or not, since the method does not examine arteriosclerotic lesions per se and further it is not clearly demonstrated if there is an exact mutual relation between the estimated probability and the presence of arteriosclerotic lesions in the body examined.

For this purpose, there is a strong need for developing a new method for detecting the presence of lesions in a human body, which has a high specificity to the lesions and a high safety in applying it to the human body and can easily be carried out without skillfullness. However, up to now, there is proposed no such effective tool.

Referring now to the method for treating these diseases, it is currently adopted to administrate an agent such as heparin, warfarin as the anticoagulant or clofibrate as the decholesterolization agent or an antilipemic agent while simultaneously adopting the dietotherapy. Among the agents for treating the diseases, the antilipemic agent is used to simply lower the concentration of lipids of patients suffering from hyperlipidemia and it does not directly affect arteriosclerotic lesions. Furthermore, it is not clear whether the decrease in the lipid concentration due to the administration of an antilipemic agent is effective to treat patients suffering from arteriosclerosis or not.

From the foregoing description, it is quite clear that there is no effective therapeutic agent for curing the disease mentioned above. This is because, in the treatment proposed previously, an agent which directly affects the arteriosclerotic lesions is not used at all and such treatment is effective only to reduce the degree of risk.

Under such circumstances, there is also a strong need for developing an agent which directly affects arteriosclerotic lesions caused due to the presence of atherosclerosis.

U.S. Pat. No. 4,619,895 to S. Cubicciotti et al., disclosed a lipoprotein marker for type IV hypertriglyceridemia using a monoclonal antibody capable of specifically binding to a characteristic epitoptic site on LDL subspecies. French Patent No. 1,531,058 discloses immunochemical determination of substances specific for atherosclerosis by using a polyclonal antibody which is prepared by a method described in Med. Klin., 61, 208 (1966).

Recently, G. Kohler and C. Milstein proposed a hybridoma technique for preparing a monoclonal antibody having a specificity to a specific antigenic determinant of the sheep red cell membrane by cultivating an antibody-producing B cell hybridoma which is obtained by fusing spleen cells of mouse immunized with SRC (sheep red cell) and myeloma cells [see, Nature (Lond.), 1975, 256, 495–497]. In addition, Proc. Nath. Acad. Sci. U.S.A., 1982, 79, 7929–7933, S. C. Fujita et al. discloses that such hybridoma technique may be applied to produce monoclonal antibodies against specific materials separated from a complex mixture of immunogens.

Such hybridoma technique has drawn great attention since these reports present a high possibility to carry out diagnosis and treatment for various kinds of diseases utilizing monoclonal antibodies having a property such that it may specifically react with specific material closely correlating to an interested disease.

Then, if a monoclonal antibody which preferentially recognizes arteriosclerotic lesions and is specifically bonded to antigens originated from lesions interested are produced according to the same procedures as mentioned above (hybridoma technique), a new method for detecting the arteriosclerotic lesions and a new medicine for treating patients suffering from these diseases would be established.

Unfortunately, it is not possible to produce a monoclonal antibody from arteriosclerotic lesions according to the conventional procedure in which cells isolated from a specific tissue, for example, foam cells are used. In addition, it is considered to be more effective to use the whole lesion, in order to produce a monoclonal antibody which is specific to various kinds of lesions of arteriosclerosis. However, such procedure has not yet been developed and the monoclonal antibody specifically reacting with the arteriosclerotic lesions has not yet been proposed.

BRIEF EXPLANATION OF THE INVENTION

Studies on the atherosclerosis to solve the problems accompanied by the conventional methods for detecting and treating diseases due to the presence of atherosclerosis have been conducted by the inventors of the present invention and it has been found that certain kinds of monoclonal antibodies have a high specificity to lesions of sclerosis and recognizes a material present within the lesions as the antigen thereof and is preferentially bonded thereto.

A principal purpose of this invention is to provide a new monoclonal antibody capable of preferentially recognizing vascular lesional sites of arteriosclerosis.

Another purpose of this invention is to provide a method for preparing such monoclonal antibody which permits the detection of the presence of sclerosis within vascular lesions thereof and the treatment of such sclerosis.

A further purpose of this invention is to provide a therapeutic agent for diseases originated from the presence of atherosclerosis.

These and other purposes of this invention can be accomplished by providing a monoclonal antibody which can specifically recognize lesional sites of arteriosclerosis and bond to the site which acts as the antigen thereto, this antibody being able to be synthesized according to a process which comprises culturing a hybridoma obtained by fusing myeloma cells and cells capable of producing antibody against arteriosclerotic lesions.

In addition, according to the present invention, an agent for detecting the presence of arteriosclerotic lesions in the arteries of a body examined and for treating patients suffering from arteriosclerosis is provided and it comprises at least one of monoclonal antibodies obtained according to the method described above.

According to the present invention a monoclonal antibody is provided which is capable of specifically recognizing arteriosclerotic lesions and which react at least neither with LDL nor with glycoproteins which have a molecular weight of more than 20,000 and which have glycose components comprising mannose, glaactose, glycosamine and galactosamine.

The monoclonal antibodies according to the present invention are completely different from the polyclonal antibodies described in the above noted French patent because the polyclonal antibodies disclosed in that patent react with glycoprotein obtained from tunica media and also recognize the glycoprotein having mannose, galactose, glycosamine and galactosamine as glycose components, while the monoclonal antibody according to the present invention neither react with the glycoprotein nor recognize glycoprotein.

BRIEF DESCRIPTION OF THE DRAWINGS

The monoclonal antibody according to the present invention will now be explained in more detail referring to the accompanying drawings in which:

FIGS. 1 to 9 are micrographs which show the conditions of an arteriosclerotic lesion or the state of an atherosclerotic lesion associated with a monoclonal antibody according to the present invention or the comparative example. (a) in each figure is a micrograph obtained by immunofluorescence microscopy, while (b) is a micrograph obtained by phase contrast microscope;

DETAILED EXPLANATION OF THE INVENTION

The monoclonal antibody according to the present invention can be obtained by cultivating hybridomas. In preparing the hybridoma, congenital arteriosclerotic mammals from which the antigen is collected are needed and the preferred examples of such mammals are WHHL rabbits since the arteriosclerosis thereof is quite similar to that of the human arteriosclerosis. Any one of lesions (cells) of arteriosclerosis may be used as the antigen for sensitizing spleen cells of mouse, however, atheroma or foam cells are most preferred examples in the light of the treatment and diagnosis for human arteriosclerosis. Fragments of these lesions are removed from, for instance, intima or media of atherosclerotic aorta and pieces of these tissues are homogenized in a suitable medium such as 0.25M SVE (0.25M sucrose, 1 mM versene and 0.1% ethanol) using a homogenizer such as polytron homogenizer to form homogenate. The homogenate is filtered to remove connective tissues and then treated with a delipidating agent such as VE (versene and ethanol) to remove lipids by fractionating the homogenate and delipidating agent. The resulting protein fraction is treated with an organic solvent such as acetone to form precipitates and the treated precipitates is then suspended in a suitable buffer solution such as PBS (phosphate buffered saline) and used in the subsequent step as antigen solution.

It is necessary to prepare sensitized spleen cells of mammals. For this purpose, mice such as BALB/c mice and rats are preferred, while preferred examples of cells sensitized with the antigen obtained above are peripheral lymphocyte of thymus and peripheral vascular cells other than spleen cells mentioned above. In the following fusion procedure, preferred myeloma cells are originated from BALA/c mice, which provide a stable hybridoma with the sensitized spleen cells or so, therefore, the preferred the mouse is a BALB/c mouse which is desirable in the light of its immune responsibility with the myeloma cells used.

Thus, the mouse is immunized with the antigen (or arterial wall) prepared above and desired tissues are removed from the sensitized mouse, which are used as one of the starting cells to form fused cells. Then, the cells, such as spleen cells, are fused with myeloma cells such as P3/UI of a BALB/c mouse to form hybridoma, according to a standard procedure disclosed in "Selected Methods in Cellular Immunology, ed. B. B. Mishell and S. M. Shiigi, 1980, 351-372, Freedman and Company" and the resulting hybridoma is cultured in a suitable selection medium such as HAT (hypoxanthine aminopterin and thymidine).

The monoclonal antibodies according to the present invention can be prepared by selecting clones, which preferentially react with arterial lesions, from the mixture of hybridomas obtained above and culturing the clone in a suitable culture medium.

The selection of clones may, for example, be carried out according to the following procedures. The culture medium is first assayed according to ELISA (enzyme linked immunosorbent assay) or indirect immunofluorescence microscopic technique to isolate clones specific to arteriosclerotic lesions and then antibody bearing hybridomas are cloned by a conventional cloning technique such as limiting dilution technique which is usually repeated one to several times.

For example, ELISA may be carried out using antigen solution diluted with 100 volumes of PBS and alkaline phosphatase-conjugated antimouse Ig (A+G+M) (Cappel) is used as a second antibody.

In this respect, as the antigen used in ELISA, the antigen fraction derived from the homogenate prepared above and the homogenate per se may be applied.

Alternatively, the indirect immunofluorescence microscopy technique may further be used when culture wells have rather high activity on ELISA, in which immunofluorescent staining is performed using frozen sections of, for instance, atherosclerotic and normal aorta which are usually fixed by neutral formalin immediately after autopsy. While normal aorta may be prepared from, for instance, a Japanese White rabbit.

As described above, after the assay of ELISA and/or indirect immunofluorescence microscopy technique, the product is subjected to limiting dilution to obtain a clone which can preferentially react with arteriosclerotic lesions. It may also be possible to provide hybridoma by repeating the limiting dilution technique, which is derived from a single parent cell and may continue to reproduce the antibody which is the same as that produced by the parent cell, however, it should then be demonstrated that the resulting hybridoma is surely derived from single parent cell, that is whether the antibody produced by hybridoma is the very monoclonal antibody or not.

As the cloning method other than the limiting dilution technique, a soft agar technique, a method using fibrin gel, and a method using fluorescence activated cell sorter (FACS) may, for example, be mentioned. Any one of these methods may also be applicable to the process of this invention.

According to the procedures mentioned above, eight groups of hybridoma were isolated. Arterial cells of arteriosclerotic rabbits and normal rabbits are soaked in each supernatant of culture medium obtained by culturing eight kinds of hybridomas (clones) and as a result, it is found that antibodies produced by two of them are bonded to both arteriosclerotic lesions and normal arterial cells. This means that these two antibodies present no specificity to arteriosclerotic lesions. While antibodies prepared by the remaining six of them are preferentially bonded to arteriosclerotic lesions such as atherosclerotic lesion and foam cells. Moreover, it is also observed that one of the latter group is specifically bonded to the intercellular lipid accumulating sites of artery and that two of the group are specifically bonded to foam cells.

Furthermore, some of the monoclonal antibodies prepared according to the process of this invention is verified to have an excellent cross-reacting property such that they can specifically be bonded to human arteriosclerotic lesions.

Therefore, it is quite apparent that the monoclonal antibodies according to the present invention seems to be used as agents for treating arteriosclerosis and detecting the presence of arteriosclerotic lesions in a body to be examined.

Part of the antigens which are recognized by the monoclonal antibody of this invention are delivered to blood and therefore the blood may be used as a sample for diagnosis. Such diagnosis can be carried out by collecting blood of a body to be examined, extracting serum from the blood collected, adding antibody labeled with a labeling agent such as an enzyme, a radioactive isotope, fluorescein and quantitatively or qualitatively analyzing the antigens delivered into the blood according to various kinds of methods such as immunoassay, enzyme immunoassay and thus it is possible to elucidate whether the body examined suffers from arteriosclerosis. Moreover, the degree of progression of arteriosclerosis may also be estimated exactly. Alternatively, it is also possible to elucidate the position and the size of lesions by effecting the scintigram of the artery utilizing $F(ab)_2$ chain of the antibody of this invention with which colloidal gold is associated and injected into the blood.

The antibody according to the present invention belongs to IgG and IgM and, has a titer of 1:32,000 (according to ELISA) and 1:3,200 (according to fluorescent antibody technique) expressed as the degree of dilution; the molecular weight thereof being 150,000 (IgG) and 900,000 (IgM), the optimum temperature thereof being 37° C. and the optimum pH thereof being 7.4.

Moreover, the hybridoma useful in the present invention is preferably cultured under the following conditions:

(a) Optimum proliferation condition
37° C.; pH 7.2
(b) Critical proliferation condition
Temperature: 30° to 45° C.

pH: 6.5 to 7.8

(c) Culture medium

Preferred are HY culture medium explained below and mouse ascites, however, other conventional culture medium known in the art may also be used.

The monoclonal antibodies according to the present invention may also be used to treat arteriosclerosis since the antibodies can be bonded to lesions to form an immunological complex when the antibody is injected into a blood vessel. That is, a complement is activated by such complex which has a capacity to migrate leukocyte, this causes focusing of polynuclear leukocyte and their macrophage which can be bonded to foam cells through its Fc receptor to activate phagocytosis per se. The macrophage, which phagocytoses the complex formed, is possibly delivered into blood and thus removes the lesions and causes degeneracy thereof.

It is also found that the monoclonal antibody according to the present invention also reacts with arteriosclerotic lesions obtained from human specimens. This fact is clearly demonstrated by cross-reaction clearly explained below.

Thus, the agent for detecting arteriosclerotic lesions and treating arteriosclerosis according to the present invention comprises at least one of antibodies specifically bound to arteriosclerotic lesions.

The monoclonal antibodies according to the present invention may be produced by artificially culturing the hybridoma in a suitable medium or by culturing the hybridoma peritonealy in a mouse.

The present invention will now be explained in more detail according to non-limitative examples.

EXAMPLE

1. Preparation of Antigen

Female homozygous WHHL rabbits (about 20 months old; the weight thereof being 2.8 to 3.0 Kg) were anesthetized and sacrificed and then cut open at the thorax to remove the thoracic aorta. As the atherosclerotic rabbits used to collect antigens, several rabbits were selected, which had thoracic aorta uniformly expanded and their wet weight fell within the range of from 1.0 to 1.5 g which was 2 to 3 times heavier than that of normal rabbits. Then, the tunica externa of the thoracic aorta was pealed off to obtain intima and media of thoracic aorta mainly composed of the expanded portion. The intima and media were cut into pieces of 1 to 2 mm square and the pieces were homogenized at 3000 to 5000 r.p.m. for 2 to 3 minutes by polytron homogenizer to form homogenate. These treatments were effected in 0.25M SVE (0.25M sucrose, 1 mM versene and 0.1% ethanol; pH 7.5). The amount of 0.25M SVE used was 5 to 10 ml per gram of wet weight of the pieces.

The resulting homogenate was filtered through four sheets of gauze superposed together to remove connective tissues and thereafter the filtrate was poured into centrifuge tubes and an equal volume of a solution containing 1 mM of EDTA and 0.1% of ethanol having a pH of 7.5 (the density thereof is less than that of 0.25M SVE; hereunder referred to as OVE, since sucrose is not contained) was overlaid on the filtrate to establish discontinuous density gradient and centrifuged at $220 \times g$ for 30 minutes.

According to the centrifugation, accumulated lipids having low specific gravity was extracted into OVE phase and disposed together with OVE. To the bottom fraction composed of 0.25M SVE phase containing proteins (inclusive of membranous components) were added four volumes of acetone previously cooled to $-20°$ C. under stirring and maintained at that temperature for 30 minutes.

Precipitates formed during a cooling procedure were collected by the centrifugation under $1,000 \times g$ at $0°$ C. and PBS (phosphate buffered saline) was added in an amount equal to that of 0.25M SVE to disperse the precipitates and the suspension thus obtained included 2 to 5 mg/ml of proteins and was used as antigen fraction (acetone-powder solution).

2. Preparation of Hybridoma (1) Fusion

Two female BALB/c mice (8 weeks old) were immunized with a mixed solution of the suspension containing antigens and obtained in step 1 and an equal amount of the Freund's Complete Adjuvant. The solution of the antigen was used in an amount of 0.2 ml per mouse. After 31 days, the mice were again immunized with a mixed solution of the antigen solution and the equivalent amount of the Freund's Incomplete Adjuvant. The mice immunized were further immunized with the antigen solution (0.25 ml/mouse) after 65 days. The spleen of the mice was removed, 3 days after the final (third) immunization procedure to obtain sensitized spleen cells. The number of spleen cells obtained were counted to be $4.4 \times 10^8$. The spleen cells were mixed with $4.8 \cdot 10^7$ of myeloma cells (P3/U1) previously cultured under the presence of 50% polyethyleneglycol (PEG 4,000: manufactured and sold by Merck Corporation) to fuse the spleen cell and the myeloma cell.

The mixture was then poured into 980 wells of 10 microplates having 98 holes per plate so that $4.5 \times 10^5$ spleen cells were assigned to each well. Then, according to a conventional method, the mixture was cultured in HAT (hypoxanthine, aminopterin and thymidine) selection medium to obtain hybridoma. As a result, it was observed that hybridomas grew in 974 wells among 980 wells (99%).

(2) Selection of Hybridoma

The supernatent of the culture medium including antibodies were first assayed according to enzyme immunoassay (ELISA). ELISA was carried out by adsorbing and fixing the acetone-powder solution, as antigen, diluted 33 times by the addition of PBS solution onto an immunoplate (manufactured and sold by Nunc) and contacting the supernatant from the culture medium of hybridoma with the surface of the immunoplate covered with antigens. As the second antibody, an alkaline phosphatase-conjugated antimouse Ig (M+A+G) (Cappel) separately prepared was used. Thus, the elucidation of the presence of monoclonal antibodies in the supernatant was conducted by estimating and comparing the strength of the color developed by p-unitrophenyl phosphate which is the substrate of the alkaline phosphatase. The samples examined were classified in 5 groups depending on the strength of the color developed. The two groups colored strongly (362 wells: first group consisting of 78 wells showing the highest color development and second group consisting of 284 wells showing secondary higher color development) were analyzed under microscopic observation according to indirect immunofluorescence microscopy. Among these wells, 50 wells were selected as they were preferentially stained and subjected them to subculture, then again analyzed and thus obtained 11 independent hybridomas. These hybridomas were cloned according to the limiting dilution technique.

The cloning procedure was further repeated twice and thus 8 independent clones were obtained (hereunder referred to as 201F, 212D, 212E, 305D, 403D, 510D, 809A and 904B respectively).

Hybridomas 212D, 305D, 201F and 904B are stable cell lines currently stored at Teikyo University, Kanagawa-ken, Japan and were also deposited at the Collection National de Cultures de Microorganisms (CNCM) of Institute Pasteur, 28, rue de Docteur Roux, Paris, France, on Feb. 6, 1986. The respective deposition numbers are shown hereinbelow:

cipitate immunoglobulin fraction, then the precipitates were dissolved in phosphate buffer of pH 7.4 followed by dialysis to obtain a crude solution containing immunoglobulin.

4. Specificity of Monoclonal Antibody (1) Specificity to lesions of Arteriosclerotic Rabbit Frozen sections prepared from atherosclerotic and normal aorta of 3 groups of female homozygous WHHL rabbits aged 10, 20 and 28 months, were stained with 8 culture mediums of hybridoma according to immunofluorescence (indirect fluorescent antibody technique) already explained above. The results obtained are shown in the following Table I.

TABLE I

| | | kind of Rabbit | | | | | | | |
|---|---|---|---|---|---|---|---|---|---|
| | | WHHL | | | | | Normal | | |
| | | Site of Staining | | | | | | | |
| | Hybridoma | Intercelluler Lipids Accumulated | Foam Cells | Subendothelial space | Arteriosclerotic Intima Cells | Arteriosclerotic Smooth Muscle Cells | Intima Cells | Smooth Muscle Cells | Class of Immunoglubulin |
| Example | 212D | +++ | − | − | − | − | − | − | I g G$_1$ |
| | 305D | ++ | − | ++ | − | − | − | − | I g G$_1$ |
| | 201F | − | +++ | − | − | − | − | − | I g M |
| | 904B | − | ++ | − | − | − | − | − | I g G$_1$ |
| | 510D | − | − | ++ | ± | − | − | − | I g G$_1$ |
| | 809A | − | − | ++ | ± | − | − | − | I g G$_1$ |
| Comparative | 212E | − | + | − | ++ | − | ++ | − | I g M |
| Example | 403D | − | + | − | ++ | + | ++ | + | I g M |

+: Stained.
−: Not Stained.
(The more the number of symbol +, the higher the strength of staining.)

| cell line | accession No. |
|---|---|
| 212D | I-512 |
| 305D | I-513 |
| 201F | I-514 |
| 904B | I-515--. |

In the staining operation, the immunofluorescent staining was performed using frozen sections of atherosclerotic and normal aorta which had been fixed by 10% neutral formalin immediately after autopsy. The normal aorta was prepared from a Japanese White rabbit and as the second antibody FITC (fluorescein-isothiocyanate)-conjugated antimouse IgG (H+L) (Cappel) was used. For negative control experiments, the frozen sections were stained with culture medium of myeloma P3/U1 followed by treating with the second antibody.

3. Preparation of Monoclonal Antibody (1) Culture Medium of Hybridoma

Each hybridoma obtained was cultured in HY culture medium consisting of 400 ml of DMEM, 60 ml of NCTC 100, 6 ml of MEM (non-essential amino acid), 2.8 ml of 100 mM sodium pyruvate, 60 mg of gentamicin, 79 mg of oxaloacetic acid, 120 units of insulin, 6 ml of 700 mM L-glutamin, 120 ml of FCS (Fetal Calf Serum) to form supernatant of culture medium. The supernatant was then treated with ammonium sulfate to obtain crude immunoglobulin fraction. The cultivation was carried out at 37° and pH 7.2.

(2) Mouse Ascites

Each one of the eight kinds of clones obtained above was injected in the abdominal cavity of BALB/c mice sensitized, one week before the injection, by treating them with 0.5 ml of pristan, in an amount of $1 \times 10^7$ cells/ml and propagated. Then, the ascites of the mice was collected, treated with ammonium sulfate to pre- As seen from the results listed in Table I, antibodies derived from the clones designated 212E and 403D were bonded not only to lesions but to normal intima cells and smooth muscle cells of intima, while the remaining six antibodies originated from the clones designated 212D, 305D, 201F, 904B, 510D and 809A were specifically bonded to lesions. In this respect, it was found that the antibody originated from the clone 212D was specifically bonded only to intercellular lipids accumulated, the antibodies from 201F and 904B only to foam cells and those from 510D and 809A only to the subendothelial space of atherosclerotic aorta. While the antibody derived from the clone designated 305D was preferentially bonded to both intercellular lipids accumulated and the subendothelial space of atherosclerotic aorta.

The classification of monoclonal antibodies obtained was also carried out by determining the class and subclass thereof using the immunoglobulin fraction prepared by treating supernatant of culture medium of each clone with ammonium sulfate. The class and subclass were determined according to the methods of ouchterlony and the enzyme immunoassay utilizing rabbit's antibody against antimouse Ig such as IgA, IgG$_1$, IgG$_{2a}$, IgG$_{2b}$, IgG$_3$, and IgM. The results obtained are also listed in Table I. As seen from Table I, it was confirmed that the antibodies obtained according to the present invention belong to IgG$_1$ or IgM.

The hybridoma cells prepared in the present invention may be stored, for example, by freezing the cells according to a desired temperature schedule using apparatuses such as Controlled Rate Freezer (manufactured and sold by Union Carbide Corporation) and maintaining the frozen cells at liquid nitrogen temperature.

The conditions of staining were explained in more detail referring to the accompanying drawings which show micrographs obtained by the methods of indirect immunofluorescence microscopy, (a) of each FIG., and phase contrast microscopy, (b) of each Figs.

In these figures, the thoracic artery removed from female homozygous WHHL rabbit suffering from atherosclerosis was used a as a sample and it was immersed in each monoclonal antibody solution and observed according to indirect immunofluorescent technique. In the indirect immunofluorescence technique, staining was carried out utilizing oil-red O.

Figure 1A:
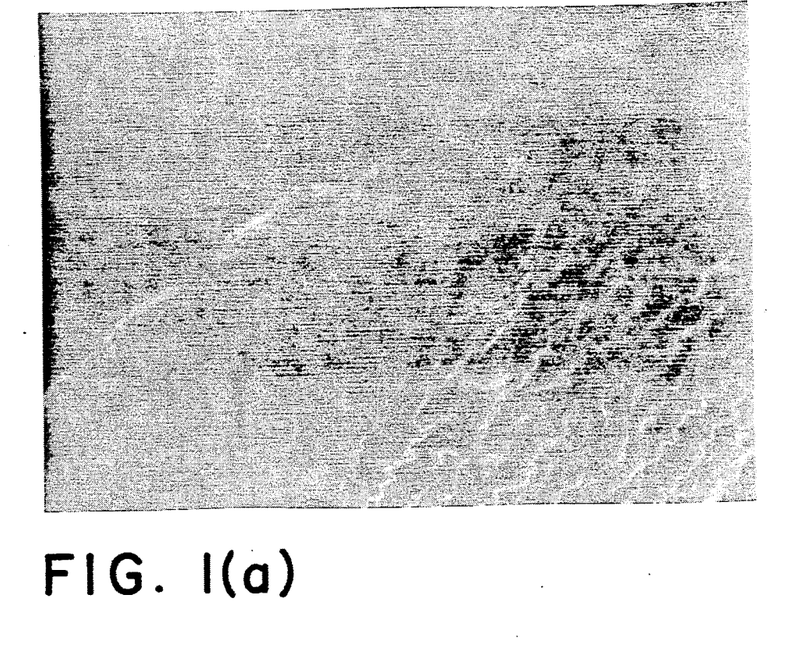
Figure 1B:
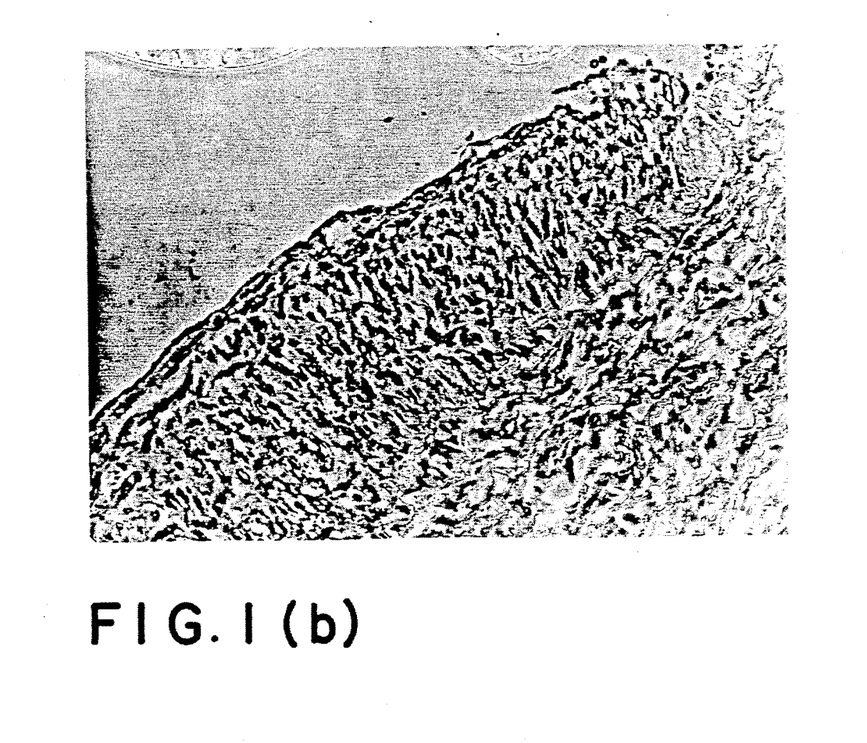

Now referring to FIGS. 1 (a) and (b), these figures show micrographs (200×magnification) of a control sample in which the supernatant of myeloma cells-culture medium is used. There is observed auto-fluorescence corresponding to the elastica at the bottom right-hand corner of the micrograph (a) and no other fluorescence is observed.

Figure 2A:
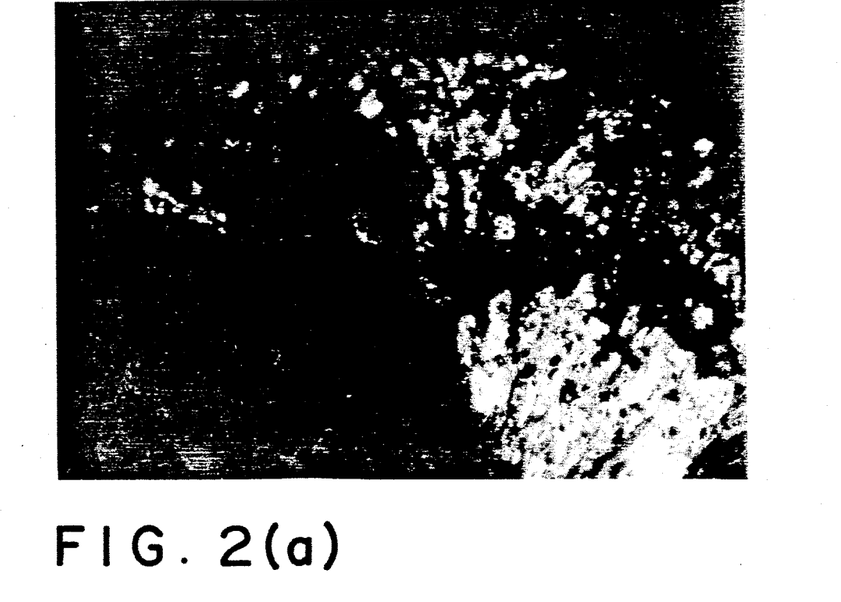
Figure 2B:
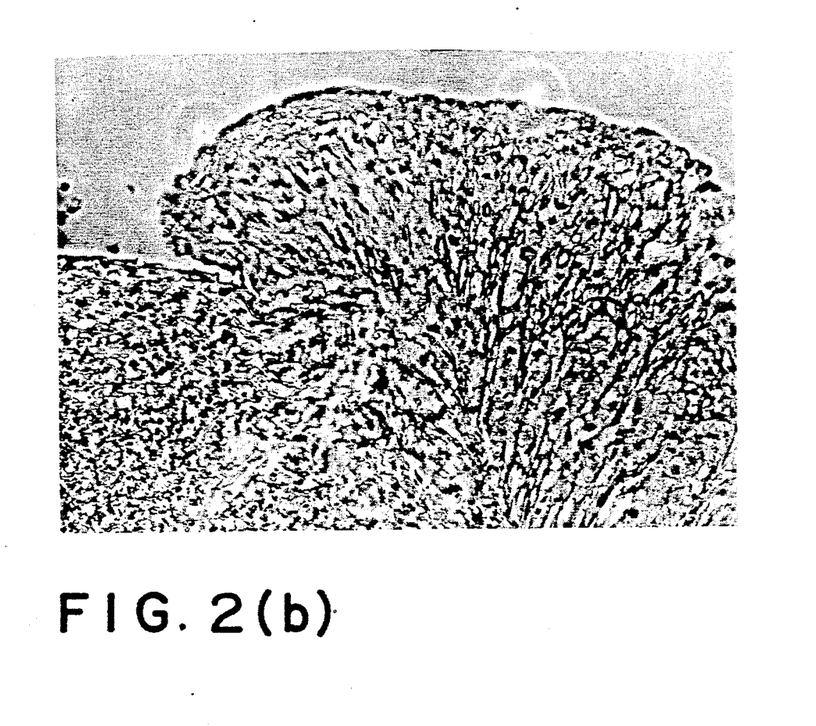

FIG. 2 (a) and (b) show micrographs (200×magnification) observed when the culture 201F is used. It is observed that in FIG. 2 (b) two layers of atherosclerotic cells are superposed with each other and foam cells extend from the boundary (at the bottom right-hand corner of the micrograph) of the layers toward the lumen. From the results shown in FIGS. 2 (a) and (b), the thoracic artery is found to be stained corresponding to the foam cells.

Figure 3A:
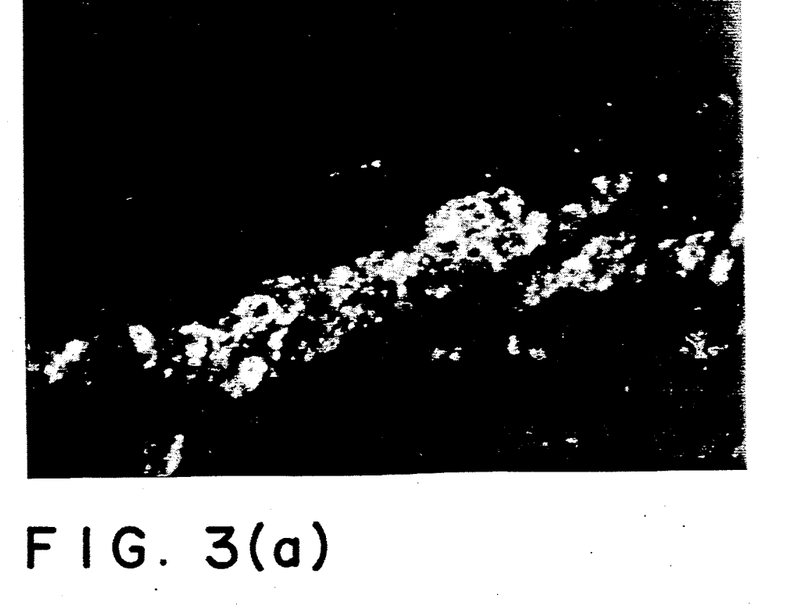
Figure 3B:
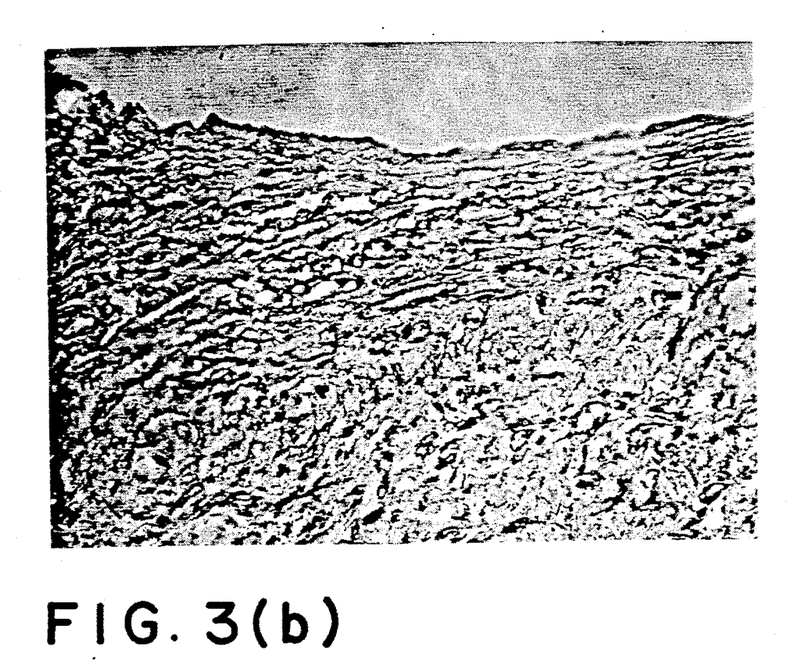

FIGS. 3 (a) and (b) show micrograph (200×magnification) obtained using the culture medium of 904B. In FIG. 3 (b), it is observed that a group of foam cells is present at the center of atherosclerotic cells. While, from the result shown in Fig 3 (a), the thoracic artery examined is found to be stained corresponding to the presence of foam cells.

Figure 4A:
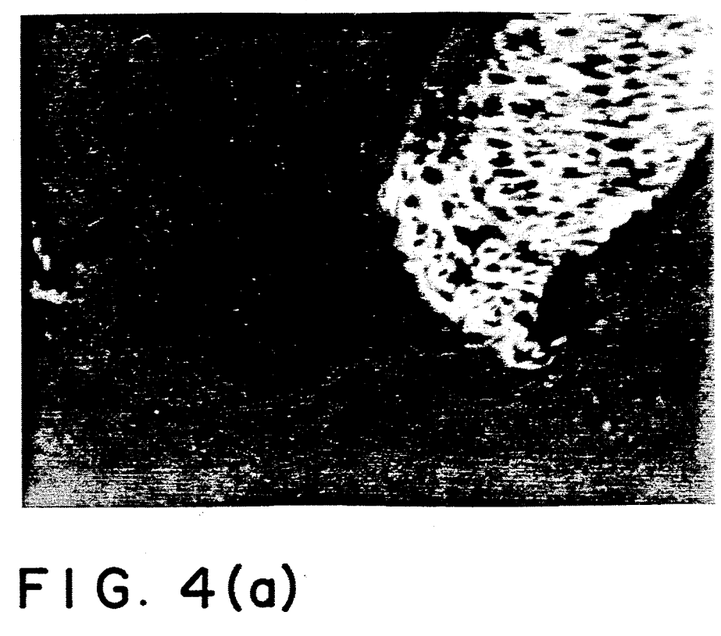
Figure 4B:
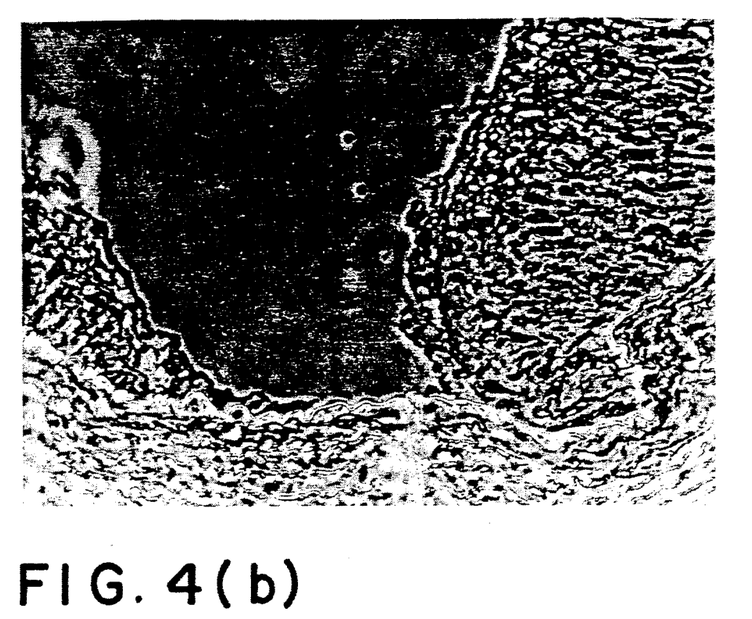

FIGS. 4 (a) and (b) show micrographs (200×magnification) obtained using the culture medium of 212D. There is observed a layer of smooth muscle at the bottom of the micrograph, see FIG. 4 (b), and there are atherosclerotic cells at both sides of the smooth muscle. The thoracic artery is found to be stained at the intercellular lipid deposits of the atherosclerotic cells existing at the right hand side of the micrograph, see FIG. 4 (a).

Figure 5A:
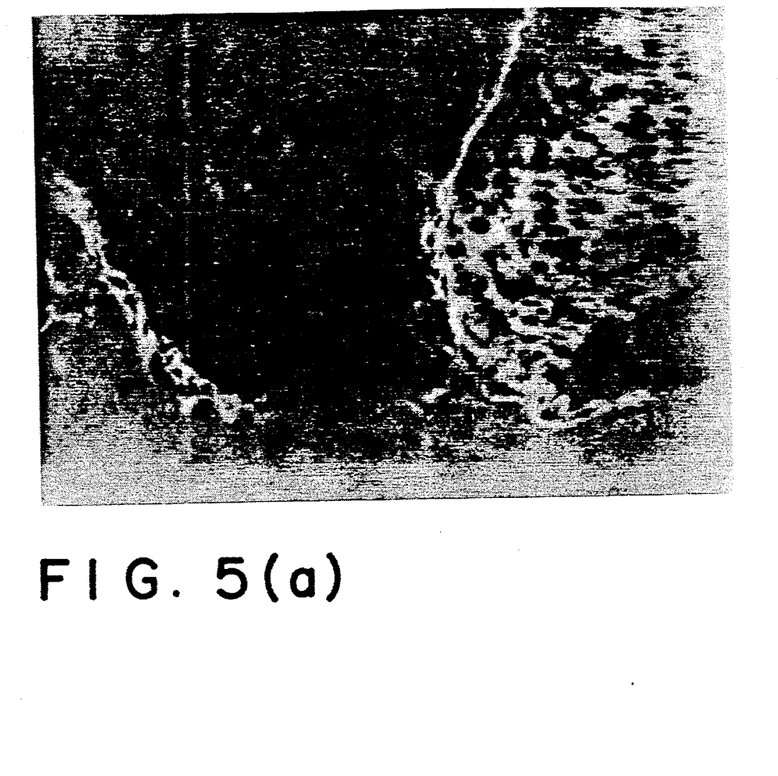
Figure 5B:
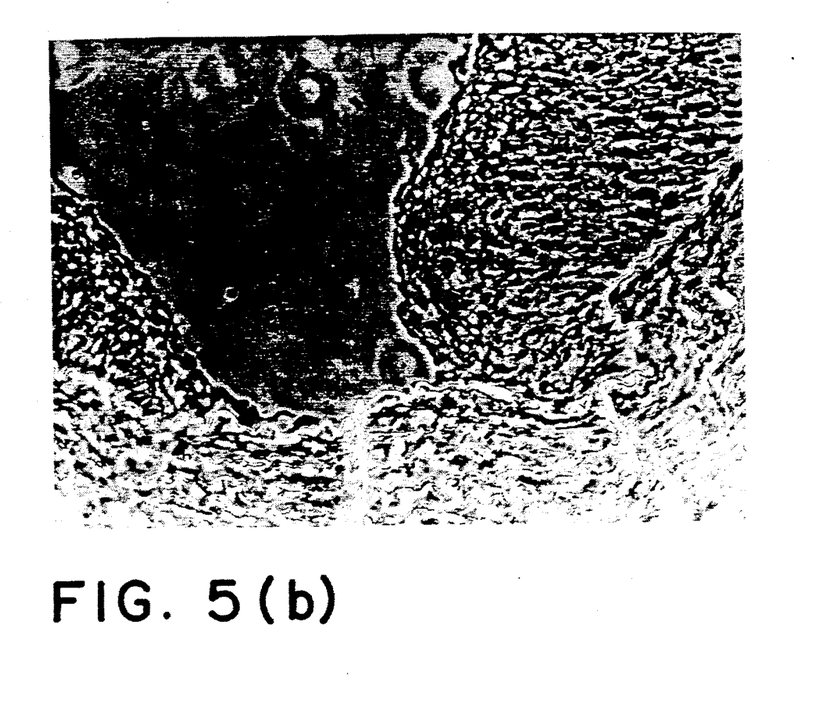

FIGS. 5 (a) and (b) show micrographs (200×magnification) observed when the culture medium of 305D is used. In FIG. 5 (b), a layer of smooth observed at the lower portion of the micrograph and atherosclerotic cells exist at both sides of the smooth muscle. It is found that the thoracic artery is stained at the same site as in the case of 212D and around the intima cells of both of the atherosclerotic cells, see FIG. 5 (a). Consequently, it is concluded that the monoclonal antibody derived from 305D differs from that derived from 212D.

Figure 6A:
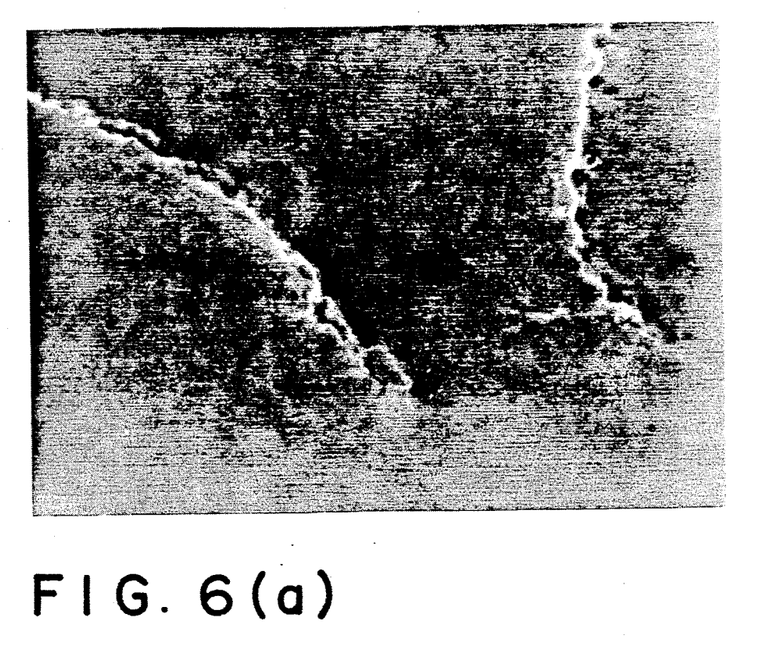
Figure 6B:
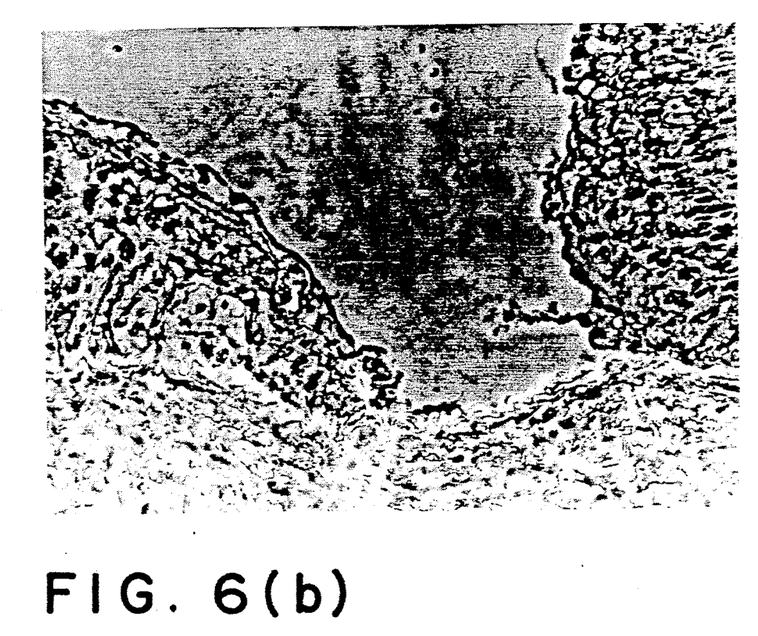

FIGS. 6 (a) and (b) show micrographs (200×magnification) obtained using the culture medium of 510D In FIG. 6 (b), atherosclerotic cells exist at both sides of the micrograph. It is concluded that the thoracic artery used is stained only around the intima cells of the atherosclerotic cells, from the result shown in FIG. 6 (a).

Figure 7A:
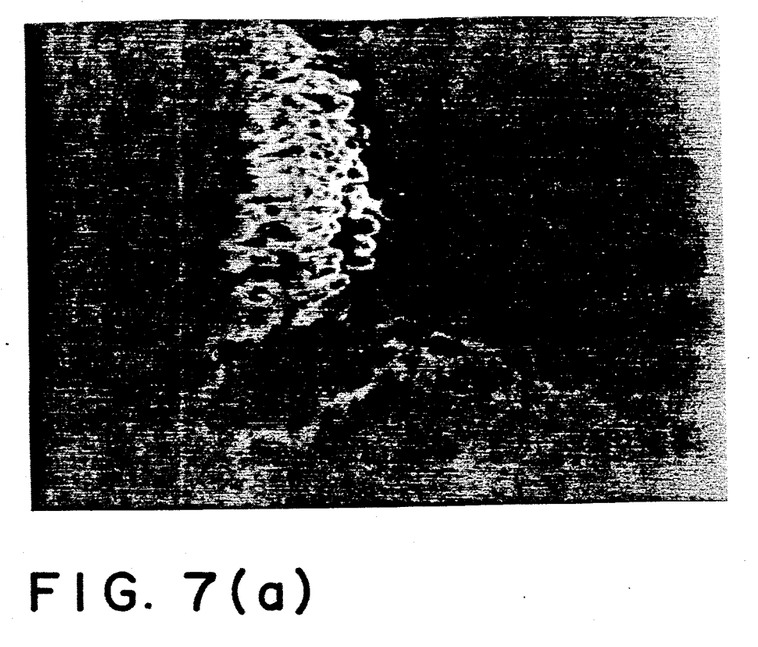
Figure 7B:
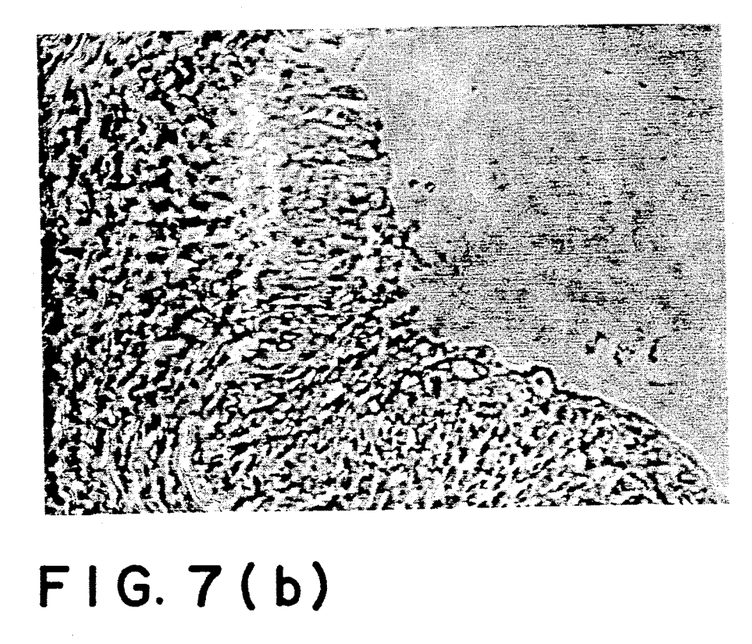

FIGS. 7 (a) and (b) show micrographs (200×magnification) obtained using the culture medium of 809A. In FIG. 7 (b), atherosclerotic cells are observed at the upper and the central part of the micrograph. While, the thoracic artery used is stained at the intercellular site existing at the extremity of the atherosclerotic cells from the result of FIG. 7 (a).

Figure 8A:
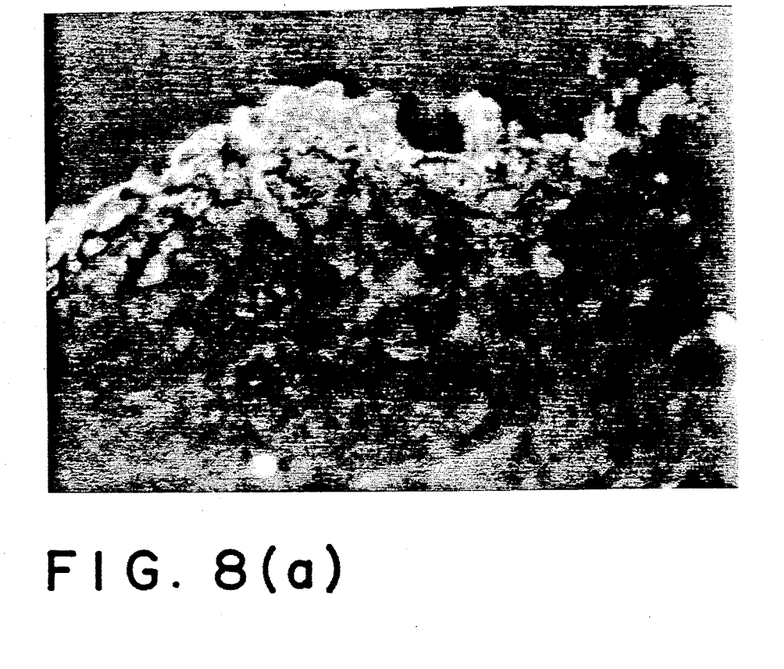
Figure 8B:
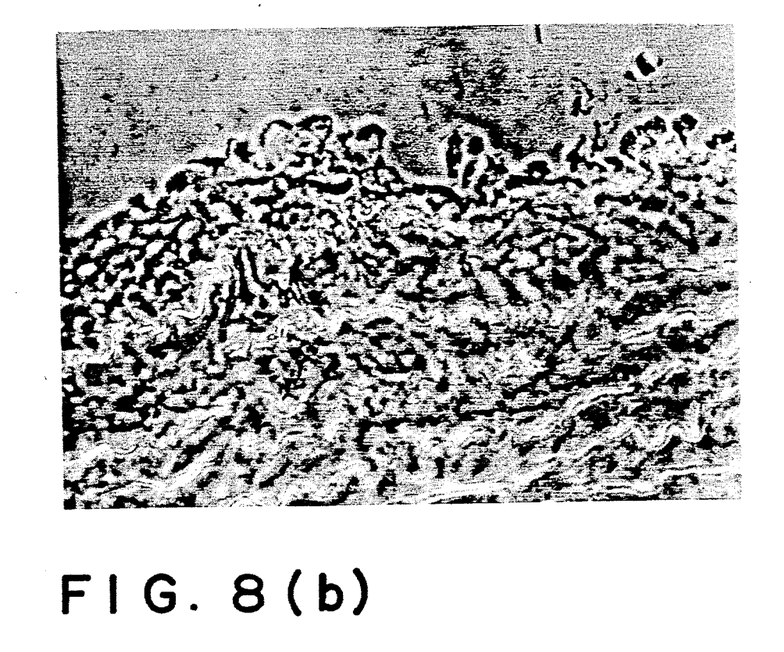

FIGS. 8 (a) and (b) show micrographs (400×magnification) obtained using the culture medium of 212E. In FIG. 8 (b), all the intima cells, foam cells and smooth muscle cells are observed and from the result shown in FIG. 8 (a), it is found that all these cells are stained.

Figure 9A:
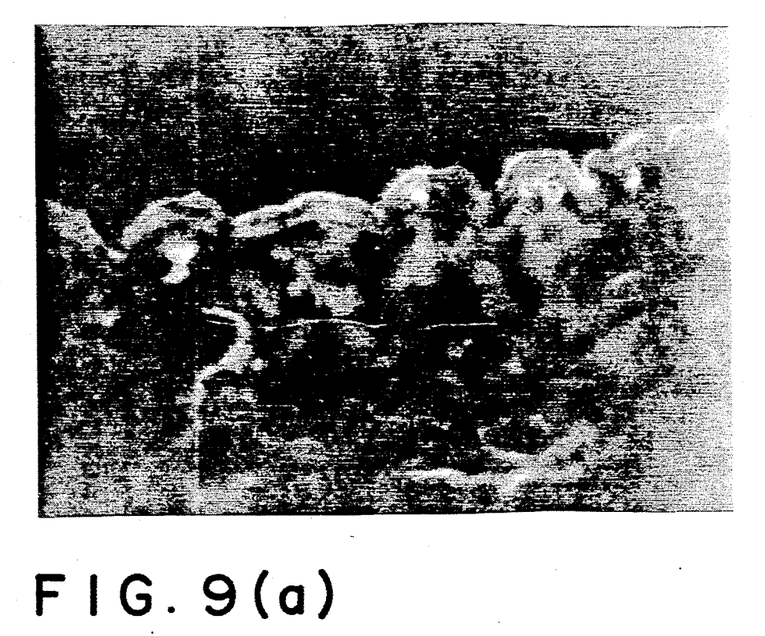
Figure 9B:
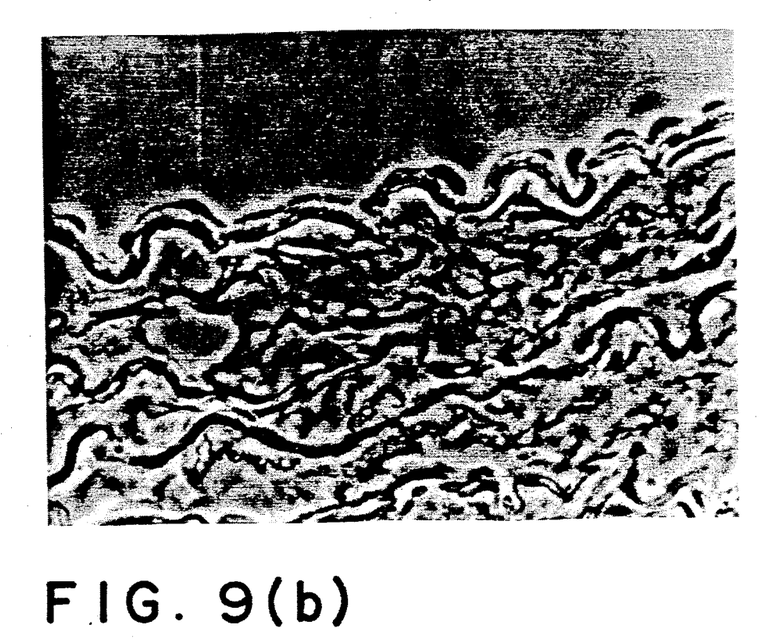

FIGS. 9 (a) and (b) show micrographs (1000×magnification) obtained when the nomal blood vessel is stained by the culture medium of 212E. It is found that nomal intima cells and a part of media cells are stained from FIG. 9 (a).

From the results of FIGS. 8 and 9, the comparative monoclonal antibody originated from the clone 212E reacts with not only the lesions of arteriosclerosis but the nomal blood vessel and therefore, this monoclonal antibody has no specificity to lesions of arteriosclerosis.

Figure 10A:
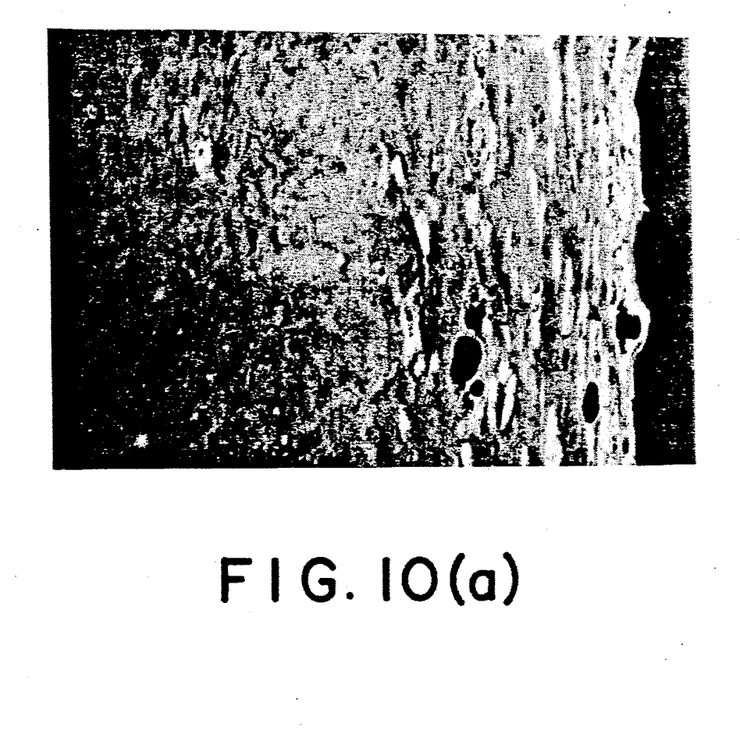
FIG. 10 is a micrograph which shows the result of the cross-reaction with human specimens.
Figure 10B:
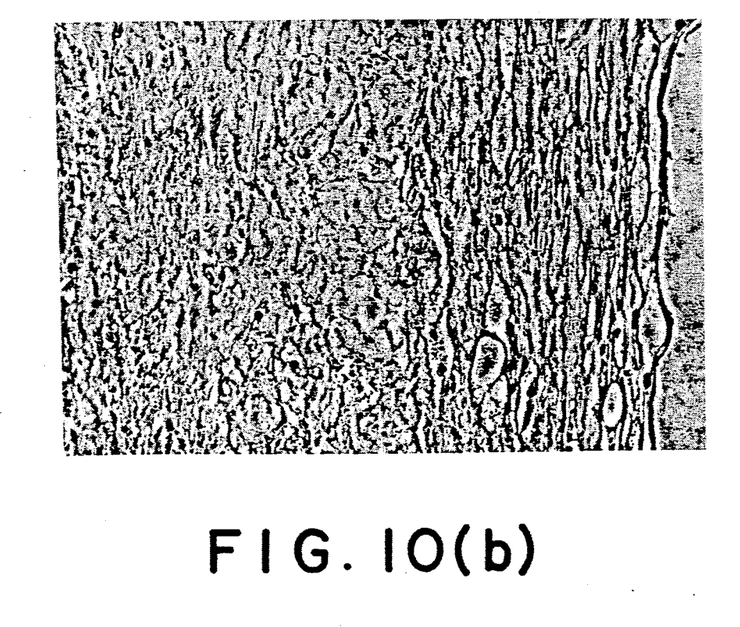

Finally, FIGS. 10 (a) and (b) show micrographs (200×magnification) obtained using human coronary artery which is stained with the monoclonal antibody derived from the clone 201F of rabbit. These results clearly show that the human coronary artery is also stained specifically at the lesions of arteriosclerosis and thus it is concluded that the monoclonal antibodies according to the present invention can surely be used as the agent for detecting and treating lesions of human arteriosclerosis.

In order to clarify characteristics of the monoclonal antibodies of the present invention, the distribution of molecular weight of antigenic material with which the monoclonal antibodies of the present invention react was determined by the gel electrophoresis (SDS-PAGE) technique and an immunoblot (Western blot) Test and also the antigen activity was determined.

Figure 11:
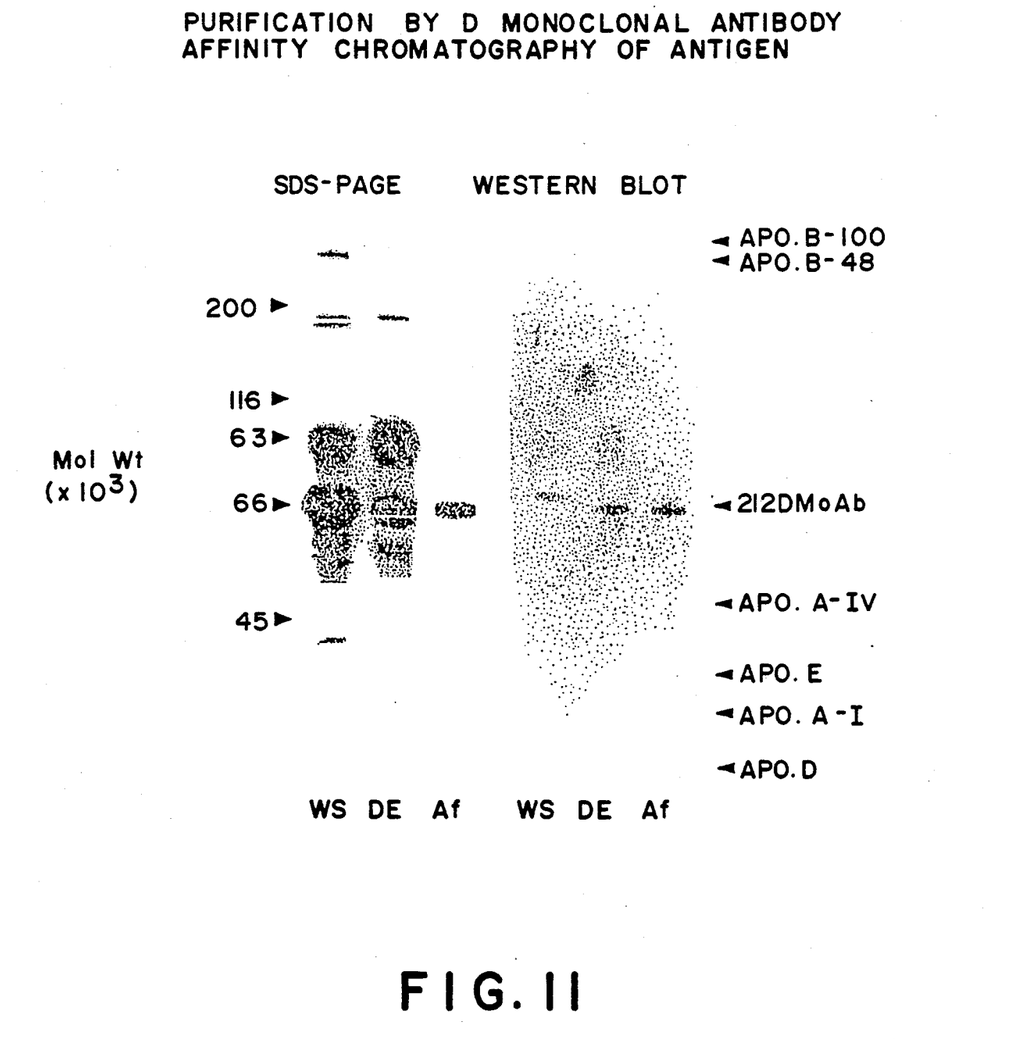
FIG. 11 shows copies from photographs of a gel electrophoresis (SDS-PAGE) and immunoblot (Western blot) test illustrating the distribution in molecular weight of antigens which are recognized by a monoclonal antibody obtained from a hybridoma 212D according to the present invention.

FIG. 11 is a drawing copied from photographs of the result of a gel electrophoresis (SDS-PAGE) and an immunoblot (Western blot) Test which show the distribution in molecular weight of antigens recognized by a monoclonal antibody obtained from the hybridoma 212D according to the present invention. Samples were prepared as following:

WHHL rabbit serum was fractionated on a carrier of polyacrylamide gel under the presence of sodium dodecysulfonate and the resulting fractions of proteins were transferred onto a cellulose acetate film. Then, an monoclonal antibody EMR1a/212D according to the present invention was reacted with the cellulose acetate film. After enough washing, antibodies which reacted with the antigens were determined with secondary antibody labelled with alkaliphosphotase.

It is apparent from FIG. 11, that (1) antigenic materials recognized by the monoclonal antibody EMR-1a/212D according to the present invention did not react with the following apoproteins;

B-100, B-48, A-IV, E, A-1 and D which are components of lipoprotein, and (2) the antigenic material have a molecular weight of 66,000.

Figure 12:
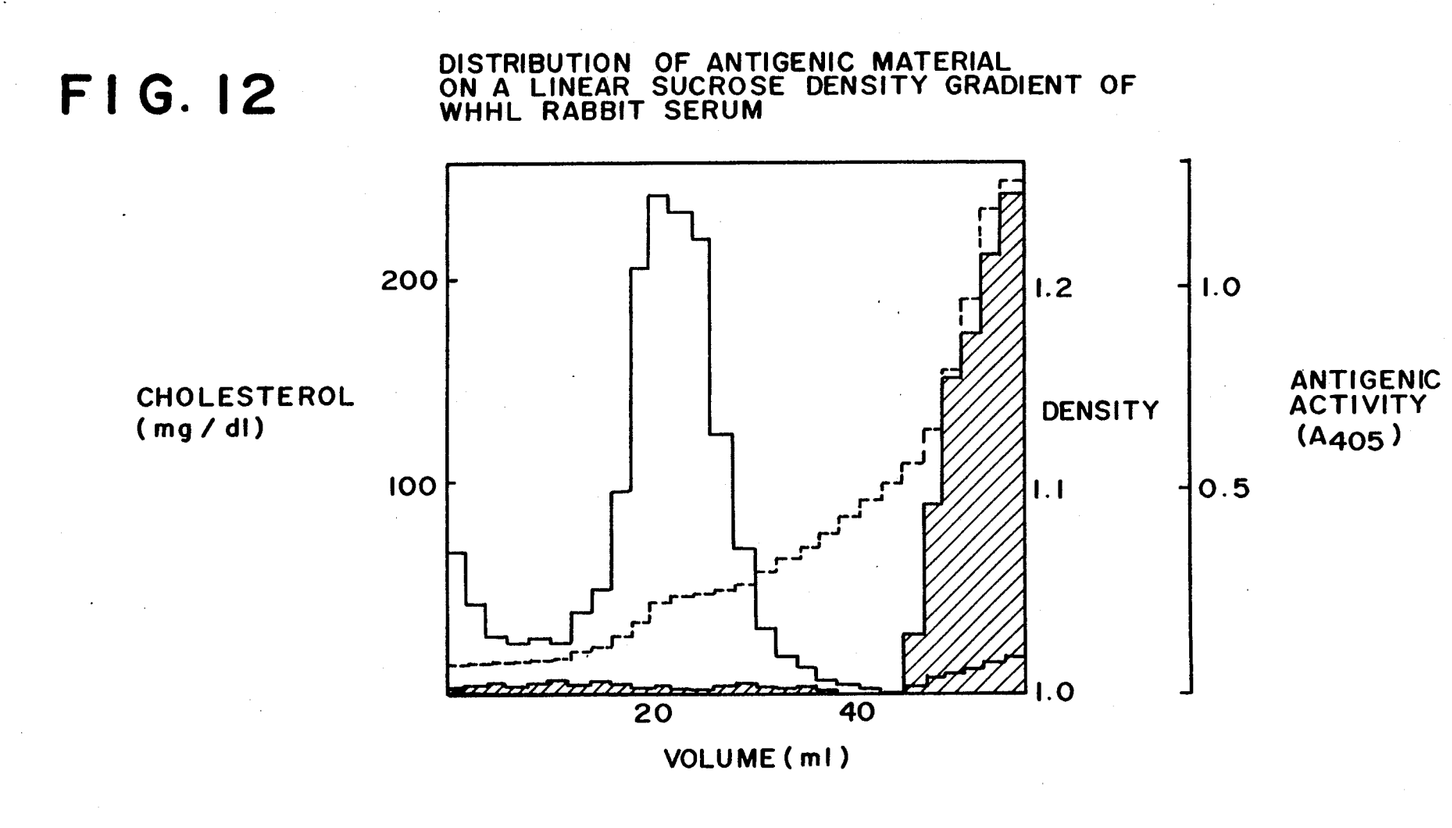
FIG. 12 shows a relationship between the distribution of antigenic material on a linear sucrose density gradient of WHHL serum and the result of ELISA illustrating the antigen activity of antigens which are reactive with the monoclonal antibody obtained from the hybridoma 212D according to the present invention.

FIG. 12 illustrates a relationship between the distribution of antigenic material in a linear sucrose density gradient of WHHL serum and the result of ELISA, which illustrates the antigen activity of antigens which reacted with the monoclonal antibody EMR1a/212D according to the present invention. Samples were prepared as following:

WHHL rabbit serum was fractionated by a density-gradient centrifugation method with NaBr. The dotted line in FIG. 12 shows the density of the density gradient liquid, while the solid line above the distribution of the antigenic materials in the density-gradient liquid. The densities of lipoprotein (VLDL, IDL, LDL, HDL) are as follows:

VLDL: 0.95–1.006, IDL: 1.006–1.019,

LDL: 1.019–1.063, HDL: 1.063–1.21

FIG. 12 also shows the result of antigenic activity of the monoclonal antibody according to the present invention determined by ELISA as a hatched graph.

It is apparent from FIG. 12 that material which was recognized by the monoclonal antibody EMR1a/212D was not the lipoprotein, because two peaks of the solid line showing the existence of cholesterol (lipoprotein) in the antigenic materials and the hatched graph showing the antigenic activity of the monoclonal antibody ERM1a/212D by ELISA are not conincident with each other.

The other three monoclonal antibodies obtained from hybridomas 305D, 201F and 904B were also subjected to the same analysis as described above and shows the same result as the case of the monoclonal antibody EMR1a/212D.

In conclusion, the above-mentioned results reveal that the monoclonal antibodies obtained from the hybridomas 212D, 305D,. 201F and 904B do not react with glycoprotein derived from tunica media.

What is claimed is:

1. Hybridoma 212D accession No. C.N.C.M. I-512.
2. Hybridoma 305D accession No. C.N.C.M. I-513.
3. Hybridoma 201F accession No. C.N.C.M. I-514.
4. Hybridoma 904B accession No. C.N.C.M. I-515.
5. An antibody derived from hybridoma 212D cell line accession No. C.N.C.M. No. I-512.
6. An antibody derived from hybridoma 305D cell line accession No. C.N.C.M. No. I-513.
7. An antibody derived from hybridoma 201F cell line accession No. C.N.C.M. No. I-514.
8. An antibody derived from hybridoma 904B cell line accession No. C.N.C.M. No. I-515.

* * * * *